United States Patent [19]

Mordwinkin

[11] 4,059,795
[45] Nov. 22, 1977

[54] DIGITAL EDDY CURRENT APPARATUS FOR SENSING AND ANALYZING METALLURGICAL CHARACTERISTICS OF AN ELECTRICALLY CONDUCTIVE MATERIAL

[75] Inventor: George Mordwinkin, Scottdale, Pa.

[73] Assignee: Sensor Corporation, Scottdale, Pa.

[21] Appl. No.: 692,481

[22] Filed: June 3, 1976

[51] Int. Cl.² .......................................... G01R 33/12
[52] U.S. Cl. .................................................. 324/233
[58] Field of Search ................................. 324/40, 37

[56] References Cited

U.S. PATENT DOCUMENTS

| 3,314,006 | 4/1967 | Hentschel | 324/40 |
| 3,391,336 | 7/1968 | Hentschel | 324/40 |
| 3,416,071 | 12/1968 | Wiers | 324/40 |

Primary Examiner—Robert J. Corcoran

Attorney, Agent, or Firm—Buell, Blenko & Ziesenheim

[57] ABSTRACT

A digital eddy current apparatus for sensing and analyzing metallurgical characteristics of an electrically conductive material. A square wave is supplied to a resonating circuit which includes a coil used as a sensing element for the conductive material. The resonating circuit produces a sinusoidal wave which is converted into a rectangular pulse which, when the resonating means is at resonance condition superimposed upon the square wave pulse it would be positioned in the center of one-half of the square wave. The width of the rectangular pulse is a direct function of the amplitude of the sinusoidal wave and phase shift of the sinusoidal waveform is detected by movement of the rectangular pulse from the center position within the square wave. The width and position of the rectangular pulse is a direct function of the metallurgical characteristics of the conductive material.

8 Claims, 7 Drawing Figures

OSCILLATOR & DRIVER CIRCUIT
FIGURE 1

PHASE & AMPLITUDE DISCRIMINATORS
BLOCK DIAGRAM

FIGURE 6

"METALANALYZER"

FIGURE 7

DIGITAL EDDY CURRENT APPARATUS FOR SENSING AND ANALYZING METALLURGICAL CHARACTERISTICS OF AN ELECTRICALLY CONDUCTIVE MATERIAL

This invention relates to a digital eddy current apparatus for non-destructive analyzing of metals.

THE PROBLEM AND THE PRIOR ART

Eddy current testing equipment is well known. It provides a non-destructive test for characteristics of conductive metals. Characteristics such as alloy, hardness, flaws and temperature have known eddy current characteristics. These eddy current characteristics can be sensed and analyzed. The eddy current characteristics can then be used to provide the metallurgical characteristics of the conductive material.

The existing eddy current testing devices do not provide a means for recording absolute data. The existing devices require more time to acquire and process the information. This is a substantial factor when instantaneous readings or data are necessary. The existing equipment does not present the information in a form which can be digitized and used in a computer for instant analysis of the metal characteristics or digitally displayed. Methods used with conventional eddy current metal testers usually consist of displaying the phase change in an oscilloscope series for reference only. Amplitude information is converted into analog voltage which is used for sorting purposes.

My invention solves the problem of time and use of absolute data by using a digital technique. It provides the capability to make corrections due to variables such as temperature of the material tested.

STATEMENT OF THE INVENTION

The presence of a metallic object or any other electrically conductive material in the A.C. magnetic field of an inductive sensing element will cause changes in its impedance, due to the eddy current effects.

My invention provides a resonating circuit having a coil. The coil acts as the sensing element. The presence of the conductive material tested (sometimes referred to as the target) is brought in proximity at a predetermined air gap to the coil. The induced eddy current in the target changes the impedance of the coil and causes a resulting change in the output of the resonating circuit. The output is then converted to a rectangular pulse.

The width of the pulse is a function of the amplitude of the output of the resonating circuit. The phase of the pulse is a direct function of the phase of the output of the resonating circuit. The phase and the amplitude correspond to a particular eddy current characteristic which can be used to determine the metallurgical characteristics of the metal target. The rectangular pulse can be digitized and used in a computer or in a digital display.

All data processing is performed at the rate of the sensing frequency, usually 10 KHz. Because of this, the method is applicable for continuous "in process" control. When used in conjunction with a computer it can be used simultaneously with a number of process control points.

I provide a digital eddy current apparatus for sensing and analyzing metallurgical characteristics of an electrically conductive material comprising a driving means supplying a square wave pulse; a resonating means coupled to the driving means, the resonating means having a sensing element with an impedance which varies depending upon an eddy current characteristics of the electrically conductive material, the resonating means changes the square wave driving pulse to a sinusoidal waveform which is a function of the impedance of the sensing element; and a converting means coupled to the resonating means and converting the sinuoisdal waveform into a rectangular pulse output, when the resonating means is at a resonance condition, if the rectangular pulse were superimposed upon the square waveform it would be positioned in the center of one-half of the square wave, the width of the rectangular pulse is a direct function of the amplitude of the sinusoidal waveform, phase shift of the sinuoisdal waveform is detected by movement of the rectangular pulse from its center position within the square waveform, the width and position of the rectangular pulse is a direct function of the electrically conductive material's metallurgical characteristics which are sensed and analyzed.

All of the designations in the block diagrams are commercially available. The commercial numbers appear in the blocks. Below is a list of the designation numbers with a brief term of their function and the manufacturing source of supply.

| DESIGNATION | FUNCTION | SOURCE |
| --- | --- | --- |
| CD4007 | Inverter | RCA |
| CD4040 | Frequency Divider | RCA |
| CD4050 | Buffer | RCA |
| MC14528 | Dual Monostable Multivibrator | Motorola |
| CD4070 | Exclusive OR Gate | RCA |
| CD4093 | Schmitt Trigger | RCA |
| CD4047 | Retriggable Monostable Multivibrator | RCA |
| CD4071 | OR Gates | RCA |
| CD4081 | AND Gates | RCA |
| CD4029 | Up-Down Counter | RCA |
| F9368 | BCD-to-7 segment converter & display driver | Fairchild |
| FND500 | LED Display | Fairchild |
| CD4013 | Dual "D" Type flip-flop | RCA |
| CD4060 | Oscillator/14 Stage Divider | RCA |

DETAILED DESCRIPTION

DRIVING MEANS (2, 6 and 8)

A driving means (FIG. 1) comprises a crystal controlled oscillator 2 at 1 MHz – 10 MHz (range) frequency. This frequency is then supplied to a frequency divider circuit 6 and to a buffer 4 which then goes to another circuit. The frequency divider 6 provides a range of frequencies indicated on the figure which provides a choice of operating frequencies from 1 MHz to 1 KHz as may be required. The frequency signals are coupled to buffers 8 and produce a perfectly symmetrical square waveform 10 through resistor 12.

RESONATING MEANS (14 and 16)

Figure 1:
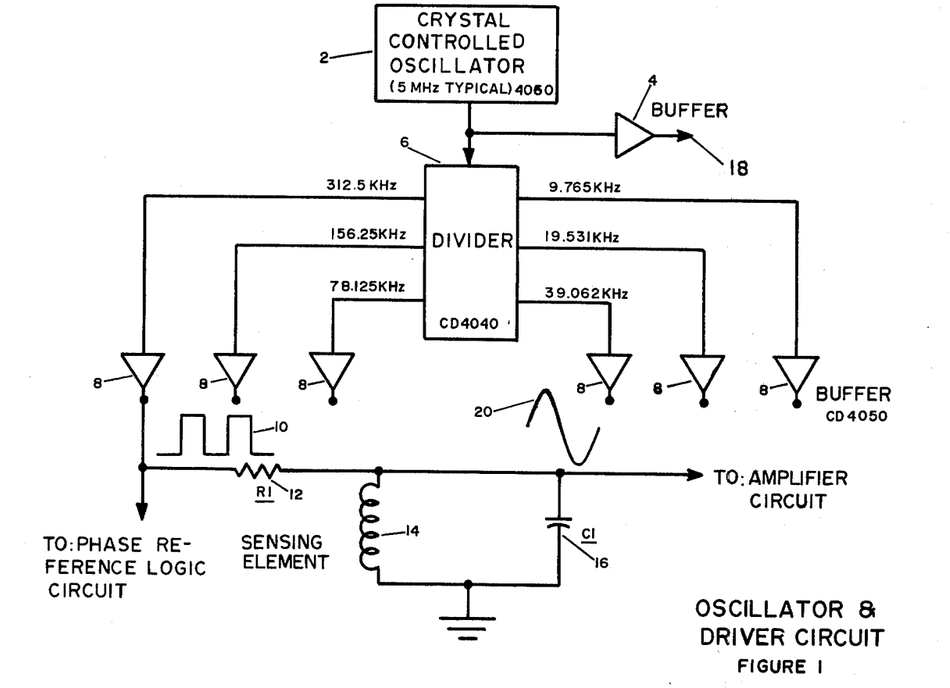
FIG. 1 is a combination block diagram and schematic.

The resonating means comprises a coil 14 which acts as a sensing element in parallel with capacitor 16.

Figure 2:
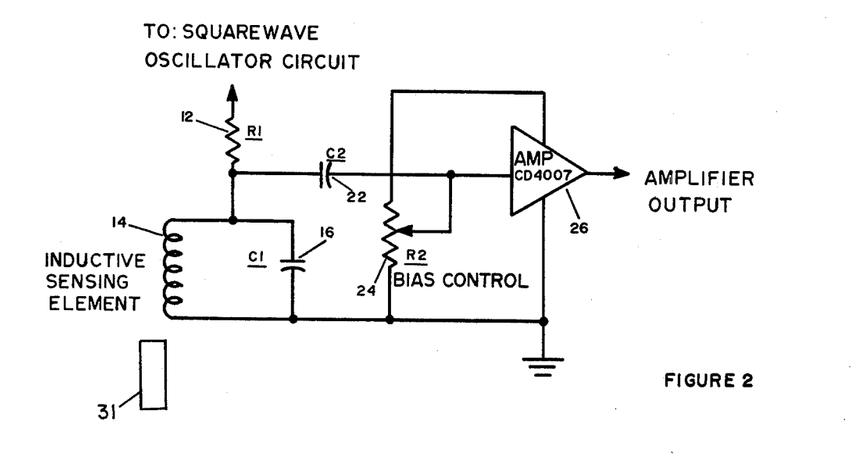
FIG. 2 is a combination block diagram and schematic.

CONVERTING MEANS (FIG. 2; references 22, 24 and 26)

The converter means comprises a coupling capacitor 22 coupled to the resonating circuit. The capacitor 22 couples the resonating circuit to an amplifier 26 having a bias control resistor 24.

OPERATION OF THE DRIVING MEANS, RESONATING MEANS AND THE CONVERTING MEANS

Figure 3:
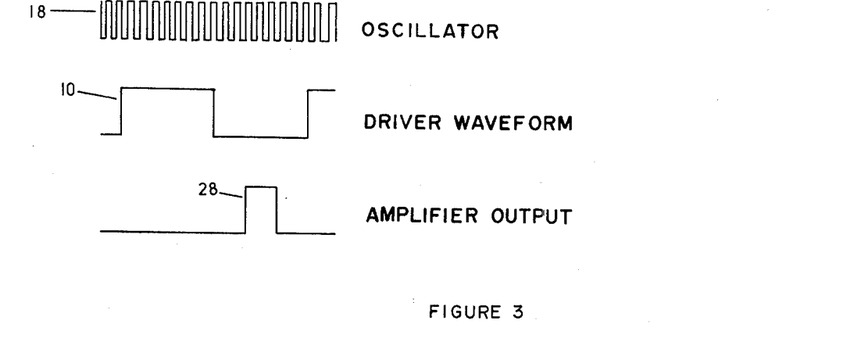
FIG. 3 shows three waveforms developed in FIGS. 1 and 2.

The oscillator 2 supplies a frequency signal 18 which is divided and applied to a buffer 8 and resistor 12. The waveform at resistor 12 is a perfectly symmetrical square waveform 10 (FIG. 3). The coil 14 and capacitor 16 operate at or near a resonance condition which provides a nearly perfect sinusoidal waveform 20. When an electrically conductive material 31 (known as metal target 31) is brought near the sensing element (coil 14) its eddy current characteristics change the impedance of the coil 14 and thus the output wave 20. The signal is then coupled to the converter circuit which includes amplifier 26.

The same waveform 10 which drives the sensing element (coil 14) is used as a phse reference to monitor the position of the sensing signal after it is processed by the converter circuit (amplifier 26).

There are a number of reasons for using a square waveform 10 to drive the coil 14 instead of the traditional sinusoidal waveform.

a. Waveform Stability

Accuracy for detection of the phase component of the sensing signal is directly related to the stability of the reference waveform 10 and, therefore, frequency and waveform symmetry between two semicycles should be absolutely perfect.

The symmetry between two semicycles is also required to prevent the instability of the sensing element 14 due to energy dissipation in the winding of the sensing element (coil 14) when two semicycles of excitation sources are non-symmetrical.

b. Amplitude Stability

Accuracy of the amplitude component detection of the sensing element (coil 14) requires a constant amplitude of the excitation source. This is easy to achieve with a square wave, but not with a sinusoidal wave.

The signal from the sensing element (coil 14) is capacitively coupled by capacitor 22 to the input of a high-gain amplifier 26. The output is a rectangular pulse 28 with the amplitude equal to the power supply voltage applied to the amplifier stage.

When the sensing element (coil 14) is at the resonance, the amplifier 26 output pulse 28 if superimposed on the square wave 10 it would be positioned exactly in the center of one-half of the square wave 10 which drives the sensing element 14 (FIG. 3). It should be noted that the resonance can be obtained either with or without the test piece (target) present adjacent the coil and it is at resonance that the output pulse 28 would be centered with the square wave 10.

Usually a negative semicycle of the sensing signal 20 is used to generate the amplifier 26 output. However, a positive semicycle can also be used when warranted.

The pulse width of the output signal 28 is directly related to the amplitude of the sensing input signal 20. Pulse width of pulse 28 increases with the amplitude of the signal 20. The sinusoidal waveform sensing signal 20 is capacitively coupled by capacitor 22 to the input of amplifier 26. The DC bias, controlled by resistor 24, performs the following functions. It determines which of the positive or negative peaks of the signal 20 is amplified by amplifier 26. It controls the intersect points between the signal wave 20 and the threshold voltage level of the input stage of amplifier 26. These intersect points determine positions of the leading and trailing edges of the output pulse 28 (output pulse 28 width).

Decreasing the amplitude of the signal 20 will change the position of the intersect points to the upper portion of the sinusoidal wave 20 and as a result the width of the output pulse 28 will decrease.

Increasing the amplitude of the sinusoidal wave 20 will lower the intersect points resulting in increasing the width of the output pulse 28.

However, when the DC bias control at resistor 24 is adjusted so that 0 axis of the sinusoidal waveform 20 is equal to the threshold voltage level of the input stage of the amplifier 26 the output pulse 28 will be a symmetrical square wave and pulse width will not change when amplitude signal 20 is changed.

Phase shift, originated in the sensing element 14, due to the eddy current effect of the metal target 31 under test is reflected by shift of the sensing output pulse 28 from the center position. Ferrous materials cause the delay of the pulse position, non-ferrous metals will advance the position of the sensing output pulse 28.

Position of the sensing output pulse 28 can also be controlled by varying a capacitance 16 connected across the sensing element 14.

Amplitude and phase shift controls are used to generate a characteristic resonance curve for the metals, called "signatures". It has been foound that when the same type of sensing element 14 is used at the same physical condition, identical "signatures" are generated only by metals of identical metallurgical characteristics, such as base alloy, impurities contents, hardness and conductivity.

Therefore, the described instrument can be utilized as a metal analyzer, when a characteristic resonance curve, decodeed into digital form, is stored in computer-type electronic memory or other similar methods and compared against unknown samples.

The circuitry previously described can be used as a metal sorting device when additional components are added. The metal sorting device can be used to compare an unkown metal with a reference signal which corresponds to a known metal. To achieve this result the following means are added.

REFERENCE MEANS (30)

Figure 4:
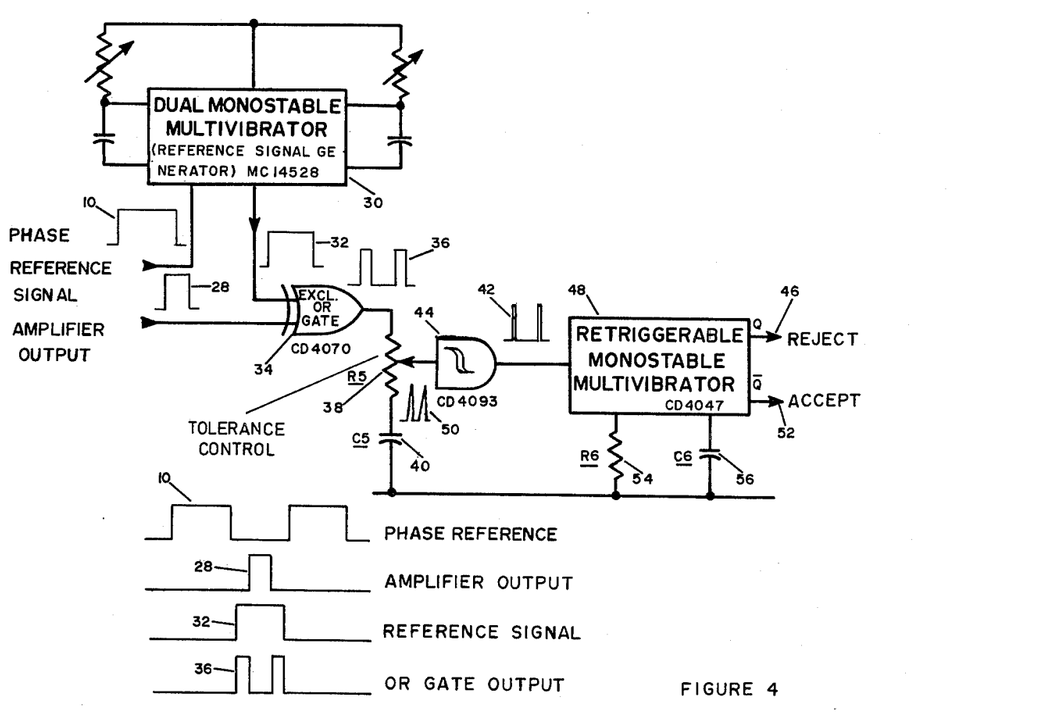
FIG. 4 is a combination block diagram, schematic and waveforms.

Referring to FIG. 4, this means comprises a dual monostable multivibrator signal generator 30 having an input square wave pulse 10 which is the same pulse that drives the resonating circuit. The generator 30 produces an output pulse 32. The function of the reference means 30 is to generate the reference signal 32, the envelope of which is compared with the envelope of the amplifier 26 output pulse 28 by means of the exclusive or gate 34. Generation of waveform 32 is initiated by the "negative-going" edge of waveform 10. The leading edge of waveform 32 is generated at the time when the timing delay, controlled by the RC network at the left is terminated. The trailing edge of the waveform 32 is generated by the second half of the dual-monostable multivibrator reference means 30 and is controlled by RC network at the right.

COMPARING MEANS (34)

The comparing means comprises a gate circuit 34.

PULSE WIDTH TOLERANCEE DISCRIMINATOR MEANS (38, 40, 44 and 48)

This means comprises a resistor 38 and a capacitor 40 which provides an RC network which is coupled to the output of gate 34. A Schmitt trigger 44 is variably coupled to the resistor 38. The output of the Schmitt trigger 44 (also referred to as a threshold detector circuit) is coupled to a retriggerable monostable multivibrator 48 which can be referred to as an AC-signal-to-output DC level-converter-circuit.

OPERATION OF THE REFERENCE MEANS; COMPARING MEANS; AND THE PULSE WIDTH TOLERANCE DISCRIMINATOR MEANS

The metal sorting device is used for sepaeration of different alloys, where precise identification of metals is not a prerequisite, but where a metallurgical match between two parts is required. This would include a selection of metal balls with the same hardness for ball bearing application, to improve the life expectancy and performance of the bearing.

This approach is substantially faster (10,000 parts/second is typical) than the conventional analog approach and more accurate than its analog counterpart, because among other additional features, it is not affected by electrical interference noise.

A reference signal 32 and the output signal 28 from the amplifier 26 are coupled to the gate 34. The output pulse 36 from the gate 34 will appear only when the pulse 28 envelope and the reference signal pulse 32 envelope are not identical.

However, when high sensitivity levels are used, only signals with exact coincidence will be acceptable thereby automatically rejecting parts which are slightly different from the reference. This situation is impractical and practical requirements call for acceptance of parts with a predetermined "percentage of deviation". Such a provision is achieved by means of potentiometer 38 and capacitor 40 which results in an RC network and controls the rise time of the pulses 50 from the gate circuit 34. This arrangement controls the threshold amplitude to the Schmitt trigger circuit 44.

When difference of the compared pulse envelopes are small, only narrow pulses are appearing at the input to a "% of deviation control" circuit which consists of tolerance control potentiometer 38, capacitor 40 and Schmitt trigger 44. When the time constant selected exceeds the width (time) of the output pulse, there will be insufficient signal amplitude to pass the Schmitt trigger circuit 44.

When the pulse width exceeds the time contant setting, controlled by potentiometer resistor 38, amplitude of the input pulse 50 will exceed the threshold level, and a pulse 42 will appear at the output terminal of the Schmitt trigger 44. The pulse 42 has a width equal to the pulse 36 from the comparing means (gate 34) minus the tolerance width set by the RC network. Pulses 42 are then applied as a trigger pulse to the retriggerable monostable multivibrator 48, the time constant of which is controlled by resistor 54 and capacitor 56, and selected to a time slightly longer than the sensing frequency. As long as trigger pulses appear at the input to the retriggerable monostable multivibrator 48, the output "Q" will continuously activate a "reject" circuit 46 (not shown). When the parts which have tolerances within the selected range, trigger pulses 42 will disappear and the terminal "Q" will switch to actuate an "accept" circuit 52 (not shown).

PULSE TO DIGITAL CONVERTER MEANS 62 AND 68 FOR DIGITALLY MEASURING THE WIDTH AND PHASE OF THE OUTPUT PULSE FROM THE CONVERTING MEANS

Figure 5:
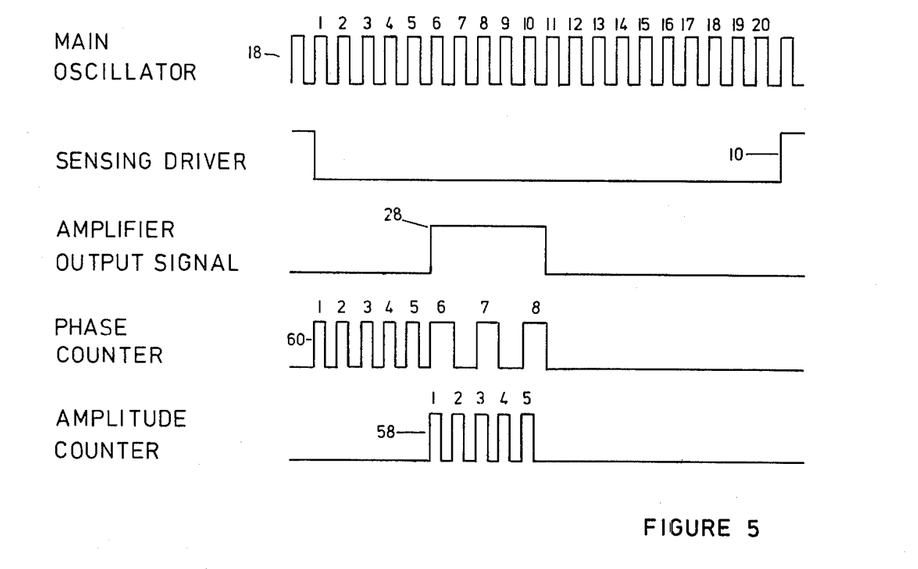
FIG. 5 is a diagram showing waveforms.
Figure 6:
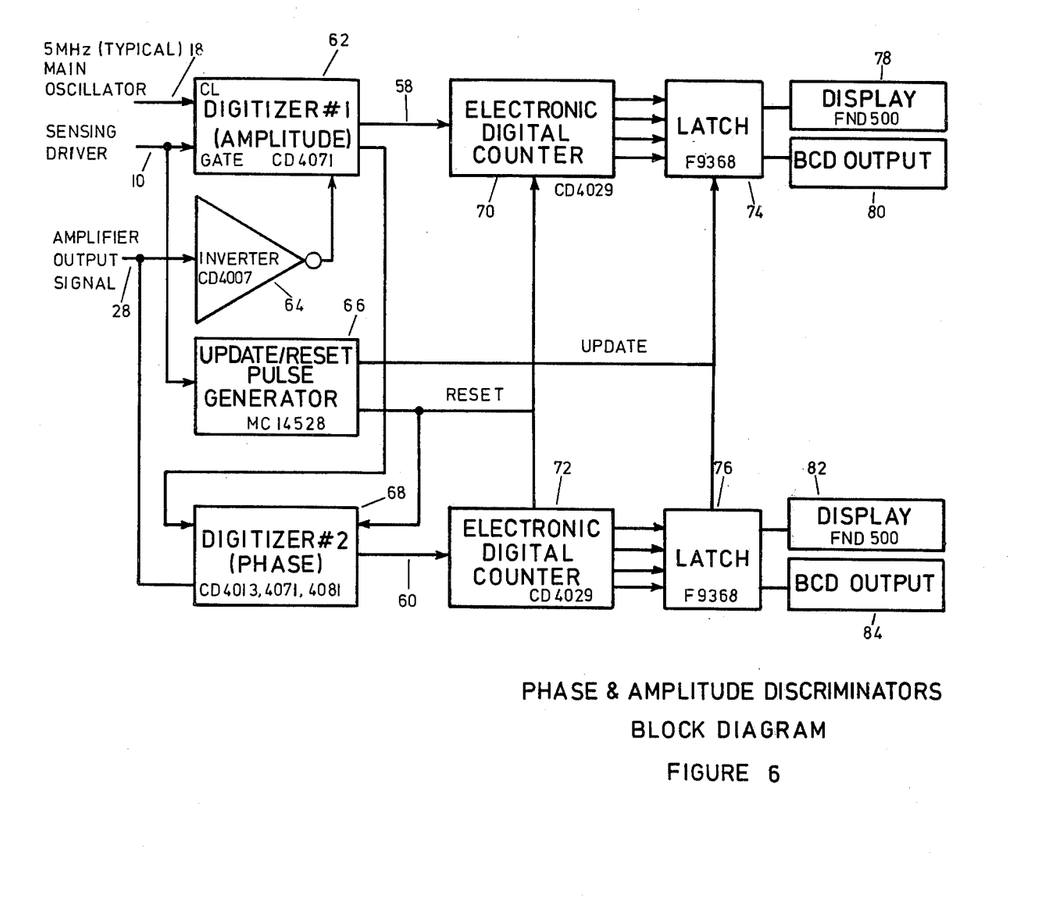
FIG. 6 is a block diagram.

Referring to FIG. 6, a pulse to digital converter means for digitally measuring the width and phase of the output pulse 28 from the converting means 26 (amplifier 26) comprises two digitizer circuits 62 and 68. Digitizer circuit 62 is coupled to the amplifier 26 through an inverter 64 which acts as an inhibitor that prevents pulses at the output of digitizer 62 except when pulse 28 is present. Digitizer 62 has inputs coupled to the buffer 4 which provides pulses 18 and to the buffer 8 which provides a symmetrical waveform 10. Digitizer 68 has an input waveform 18 from buffer 4 (FIG. 1) which is gated by digitizer 62 prior to the input of the digitizer 68 (FIG. 6). Digitizer 68 has another input from buffer 8 of waveform 10 which is processed by reset pulse generator 66 prior to input into the digitizer 68. The output pulses 58 and 60 from digitizers 62 and 68 are coupled to digital counters 70 and 72 respectively. The outputs of the counters 70 and 72 are coupled to latch circuits 74 and 76 with their outputs coupled to display and BCD output circuits 78, 82, 80 and 84 respectively. A numerical display is provided at display outputs 78 and 82 which corresponds to known "signatures" thereby providing metalurgical analysis of the metal target 31. The BCD outputs 80 and 84 can be coupled to computers for storing and processing. FIG. 5 shows a comparison of the pulse waveforms 18, 10, 28, 60 and 58.

The operation is as follows:

Amplitude digitizer circuit 62 functions as a gate which allows counting pulses 18 from the main oscillator 2 to reach the amplitude counter 70 only during the presence of pulse 28. The amplitude digitizer 62 is inhibited during the remaining cycle portion of pulse 28 by inverter 64. Waveform 10 input to the amplitude digitizer 62 blocks 5 MHZ counting pulses during non-sensing semicycle of waveform 10 and is used only to prevent a false triggering of the counter 70 but is it not essential to the operation.

Phase digitizer 68 gates counting pulses 18 from the beginning of sensing semicycle square waveform 10. When signal waveform 28 arrives, phase digitizer 68 is switched to "divide-by-two" mode which continues to the end of the pulse 28. Waveform 10 is processed by reset pulse generator 66 prior to input to the digitizer 68 and waveform 18 is gated by digitizer 62 prior to the input to the digitizer 68.

The total combined count is retained at the outputs of the amplitude and phase counters 70 and 72 until the "up date" pulse transfers this information to corresponding latches 74 and 76. Immediately following the "up date" pulse "reset" pulse is generated, which resets both counters 70 and 72. Display information is updated with every sensing cycle 28.

PULSE TO DIGITAL CONVERTING MEANS FOR DIGITALLY DECODING POSITION OF THE LEADING AND TRAILING EDGES OF THE RECTANGULAR PULSE OUTPUT FROM THE CONVERTING MEANS (26)

Figure 7:
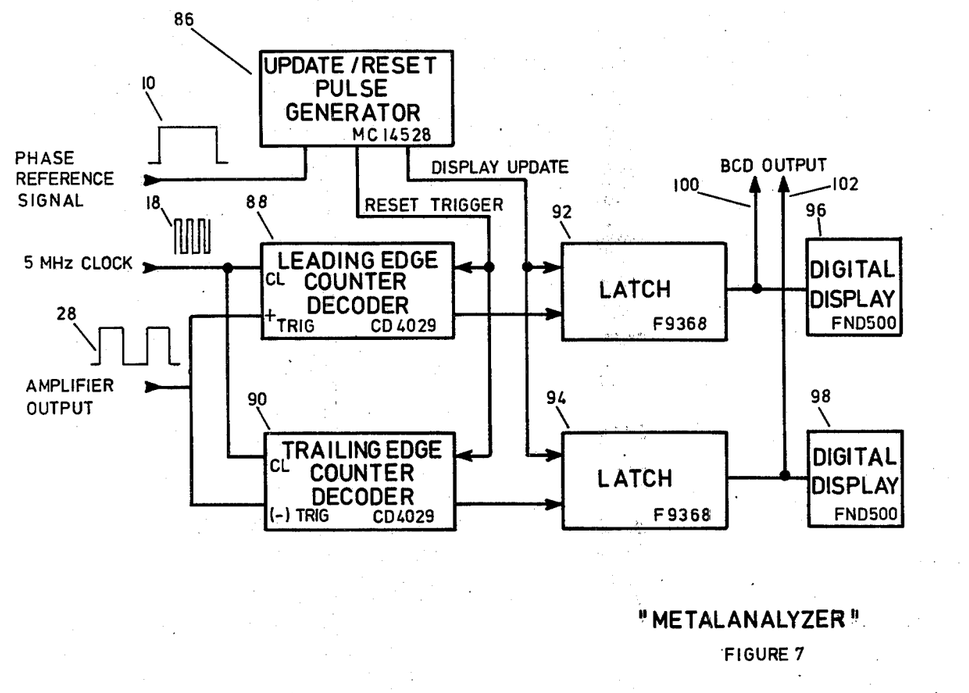
FIG. 7 is a block diagram.

Referring to FIG. 7, the pulse to digital converting means for digitally decoding position of the leading and trailing edges of the pulse output 28 from the converting means includes an up date/reset pulse generator circuit 86 coupled to the buffer 8 producing a symmetrical square waveform 10. A leading edge counter decoder 88 and trailing edge counter decoder 90 have inputs coupled to: (i) buffer 4 which produces pulse 18 and acts as a clock frequency; and (ii) converting means 26 (amplifier 26) which produces a rectangular pulse 28 which carries the metallurgical data from the metal target 31. The outputs of the leading edge counter decoder 88 and trailing edge counter decoder 90 are coupled to latch circuits 92 and 94 respectively. The outputs of the latch circuits 92 and 94 are coupled to BCD outputs and digital displays 100, 102, 96 and 98. The digital displays 96 and 98 provide a numeral reading which corresponds to "signatures" of the metal characteristics of the metal target 31. If computer storing and processing are required the BCD outputs 100 and 102 are provided.

The operation of the above circuitry is as follows. The leading edge counter/decoder 88 starts the counting of the pulses 18 from the main oscillator (or buffer 4) when the corresponding semicycle of the square wave 10 starts. When the leading edge of pulse 28 arrives, the counter 88 is stopped and the resulting count is retained at the output of the counter/decoder 88 until an up date signal is received.

The trailing edge counter/decoder 90 starts with arrival of the trailing edge of pulse 28 and counts to the end of the square wave 10.

Immediately after the end of the square wave 10, the "up date" signal will transfer the count information of both "leading" and "trailing" edge counters to the latches 92 and 94 and the new information is displayed.

Immediately following the "update" signal the "reset" signal is generated, which resets both counters 88 and 90. This procedure repeats with each sensing cycle determined by the square wave 10.

In the foregoing specification, I have set out certain preferred embodiments of my invention, however, it will be understood that this invention may be otherwise embodied within the scope of the following claims.

I claim:

1. A digital eddy current apparatus for sensing and analzying metallurgical characteristics of an electrically conductive material comprising:
   a. driving means supplying a square wave which is used as a reference;
   b. a resonating means coupled to the driving means, the resonating means having a sensing element with an impedance which varies depending upon an eddy current characteristic of the electricity conductive material, the resonating means changes the square wave to a sinusoidal waveform which is a function of the impedance of the sensing element;
   c. converting means coupled to the resonating means and converting the sinusoidal waveform produced by the resonating means into a rectangular pulse output, which pulse, when the resonating means is at a resonance condition, when referenced to the square wave pulse would be positioned in the center of one-half of the square wave, when the resonating means is magnetically coupled to the conductive material, the amplitude and phase of the sinusoidal waveform will be affected by the material characteristics, and the width and phase of the rectangular pulse will also be affected, the width of the rectangular pulse is a direct function of the amplitude of the sinusoidal waveform, movement of the rectangular pulse from its referenced position in the center of one-half of the square wave is a function of phase shift of the sinusoidal waveform; and
   d. means for monitoring the width and position of the rectangular pulse with respect to the reference square wave as a direct function of the electrically conductive material's metallurgical characteristics.

2. An apparatus as recited in claim 1 wherein the means for monitoring includes:
   reference means responsive to the square wave for providing a rectangular pulse reference output which represents a known eddy current characteristic of a known electrically conductive material and
   b. comparing means coupled to the reference means output and the output of the converting means "for comparing the width and position of the rectangular pulse to the rectangular pulse reference", if the pulse reference output from the reference means and the rectangular pulse output of the converter means are substantially identical then no signal output will be produced by the comparing means, if the pulse reference output from the reference means and the rectangular pulse output of the converter means are different then the comparing means will produce a rectangular pulse output which corresponds to the difference between the two input pulses to the comparing means.

3. An apparatus as recited in claim 1 wherein the means for monitoring includes a means coupled to the converting means for digitally measuring the width of the converting means output pulse thereby providing digital signals which correspond to the amplitude variations caused by the metallurgical characteristics of the electrically conductive material.

4. An apparatus as recited in claim 1 wherein the means for monitoring includes means coupled to the converting means output for digitally measuring the phase of the converting means output pulse relative to the reference square wave and thereby providing digital signals which correspond to the phase variations caused by the metallurgical characteristics of the electrically conductive material.

5. Apparatus as recited in claim 1 wherein the means for monitoring includes a means coupled to the output of the converting means for digitally decoding position of the leading and trailing edges of the rectangular pulse output from the converting means within a semicycle of the square wave from the driving means.

6. Apparatus as recited in claim 2 including a pulse width tolerance discriminator means coupled to the output of the comparing means, the pulse width tolerance discriminator means produces a rectangular pulse output which has a width equal to the pulse output of the comparing means minus tolerance pulse width which is set by the pulse width tolerance discriminator means.

7. Apparatus as recited in claim 6 wherein the pulse width tolerance discriminator means comprises:
   a. a resistor and capacitor which provides an RC network; and
   b. a threshold detector circuit variably taped from the resistor.

8. Apparatus as recited in claim 7 including a pulse-to-DC converter means having an input coupled to an output of the threshold detector circuit, the pulse-to-DC-converter means provides a reject signal when there is an input pulse to the pulse-to-DC-converter means input and provides an accept signal output when there is no pulse to the pulse-to-DC-converter means input.

* * * * *

UNITED STATES PATENT OFFICE
CERTIFICATE OF CORRECTION

Patent No. 4,059,795          Dated November 22, 1977

Inventor(s) GEORGE MORDWINKIN

It is certified that error appears in the above-identified patent and that said Letters Patent are hereby corrected as shown below:

In the Abstract, line 8, after "condition" should read --if--.

Column 2, line 2, "impedancee" should read --impedance--.

Column 2, line 3, "characteristics" should read --characteristic--.

Column 2, line 8, "sinuoisdal" should read --sinusoidal--.

Column 2, line 15, "sinuosidal" should read --sinusoidal--.

Column 2, line 32, after "diagram;" should read --and--.

Column 3, line 22, before "as" should read --a--.

Column 3, line 29, "phse" should read --phase--.

Column 3, line 66, after "Usually" insert a comma.

Column 4, line 38, "foound" should read --found--.

Column 4, line 46, "decodeed" should read --decoded--.

Column 5, line 8, "TOLERANCEE" should read --TOLERANCE--.

Column 5, line 24, "sepaeration" should read --separation--.

Column 5, line 54, delete --a--.

UNITED STATES PATENT OFFICE
CERTIFICATE OF CORRECTION

Patent No. 4,059,795  Dated November 22, 1977

Inventor(s) GEORGE MORDWINKIN

It is certified that error appears in the above-identified patent and that said Letters Patent are hereby corrected as shown below:

Column 5, line 60, "contant" should read --constant--.

Column 6, line 37, "metalurgical" should read --metallurgical--.

Column 6, line 52, "is it" should read --it is--.

Column 6, line 66, after "pulse" insert --a--.

Column 7, Claim 1, line 60, "electricity" should read --electrically--.

Column 8, Claim 2, line 20, before "reference" should read --a.--.

Column 8, Claim 2, line 23, after "material" should read --,--.

Column 8, Claim 2, line 26, before "for" delete the quotation marks.

Column 8, Claim 2, line 28, after "reference" delete the quotation marks.

Column 8, Claim 3, line 41, after "means" should read --output--.

UNITED STATES PATENT OFFICE
CERTIFICATE OF CORRECTION

Patent No. 4,059,795            Dated November 22, 1977

Inventor(s) George Mordwinkin

It is certified that error appears in the above-identified patent and that said Letters Patent are hereby corrected as shown below:

Column 9, Claim 8, line 8, "DC converter" should read

-- DC-converter --.

Signed and Sealed this

Second Day of May 1978

[SEAL]

Attest:

RUTH C. MASON
Attesting Officer

LUTRELLE F. PARKER
Acting Commissioner of Patents and Trademarks